United States Patent
Mori et al.

(10) Patent No.: US 6,689,902 B2
(45) Date of Patent: Feb. 10, 2004

(54) ARYLPROPYL ALDEHYDE DERIVATIVES, PROCESSES FOR PRODUCING THE SAME, AND METHODS OF USING THE SAME

(75) Inventors: Kenichi Mori, Kawasaki (JP); Shigeru Kawahara, Kawasaki (JP); Tadashi Takemoto, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 46 days.

(21) Appl. No.: 10/197,808

(22) Filed: Jul. 19, 2002

(65) Prior Publication Data

US 2003/0032842 A1 Feb. 13, 2003

Related U.S. Application Data

(63) Continuation of application No. PCT/JP01/00174, filed on Jan. 12, 2001.

(30) Foreign Application Priority Data

Jan. 20, 2000 (JP) ......................................... 2000-011538

(51) Int. Cl.[7] ........................ C07C 59/00; C07C 229/00
(52) U.S. Cl. ........................... 562/465; 560/40; 560/41; 560/42
(58) Field of Search ........................... 562/465; 560/41, 560/42, 40

(56) References Cited

U.S. PATENT DOCUMENTS 5,480,668 A * 1/1996 Nofre et al. ................. 426/548

FOREIGN PATENT DOCUMENTS

| EP | 1221448 A1 * | 7/2002 |
| EP | 1223175 A1 * | 7/2002 |
| WO | WO 99/52937 | 10/1999 |
| WO | WO 00/17230 | 3/2000 |

OTHER PUBLICATIONS

*Both European patent claiming priority back to 1999 basu upon Japanese patents.*
C.M. Tice, et al., *J. Org. Chem.*, vol. 48, No. 25, pp. 5043–5048 (1983).
K. Nagayama, et al., *Chemistry Letters*, pp. 1143–1144 (1998).

* cited by examiner

*Primary Examiner*—Alan L. Rotman
*Assistant Examiner*—Hector M Reyes
(74) *Attorney, Agent, or Firm*—Oblon, Spivak, McClelland, Maier & Neustadt, P.C.

(57) ABSTRACT

3-(3-Methyl-4-hydroxyphenyl)-3-methylbutyl aldehyde may be produced from 3-(3-methyl-4-hydroxyphenyl)-3-methylbutyric acid by converting the carboxyl group into a formyl group. N-[N-[3-(3-methyl-4-hydroxyphenyl)-3-methylbutyl]-L-α-aspartyl]-L-phenylalanine 1-methyl ester, which is useful as a sweetener having a high potency of sweetness, can be easily and efficiently prepared on an industrial production from such an aldehyde derivative, via a reductive alkylation reaction with aspartame. Therefore, 3-(3-Methyl-4-hydroxyphenyl)-3-methylbutyl aldehyde is extremely excellent as an intermediate for the production of N-[N-[3-(3-methyl-4-hydroxyphenyl)-3-methylbutyl]-L-α-aspartyl]-L-phenylalanine 1-methyl ester.

The above butyric acid derivative is a novel compound, which can be easily produced by subjecting 3-(3-methyl-4-methoxyphenyl)-3-methylbutyric acid obtained by the reaction of 2-methoxytoluene with 3-methylcrotonic acid, to a reaction for converting a methoxy group into a hydroxyl group.

The present invention further provides several novel compounds useful as a production intermediate, such as the above aldehyde derivative and the like.

20 Claims, No Drawings

ARYLPROPYL ALDEHYDE DERIVATIVES, PROCESSES FOR PRODUCING THE SAME, AND METHODS OF USING THE SAME

CROSS REFERENCES TO RELATED APPLICATIONS

This application claims priority to Japanese Patent Application No. 2000-11538, filed on Jan. 20, 2000, and International Patent Application No. PCT/JP01/00174, filed on Jan. 12, 2001, both of which are incorporated herein by reference in their entireties.

BACKGROUND OF THE INVENTION

1. Field of the Invention

The present invention relates to novel arylpropyl aldehyde derivatives which are useful as production intermediates for food products, pharmaceutical products, and the like, and in particular for the production of N-[N-[3-(3-methyl-4-hydroxyphenyl)-3-methylbutyl]-L-α-aspartyl]-L-phenylalanine 1-methyl ester, which is excellent as a sweetener having a high potency of sweetness. The present invention also relates to novel processes for the production of such intermediates. The present invention further relates to novel processes for the production of N-[N-[3-(3-methyl-4-hydroxyphenyl)-3-methylbutyl]-L-α-aspartyl]-L-phenylalanine 1-methyl ester.

2. Discussion of the Background

In recent years, as eating habits and diet have improved to a high level, obesity caused by excessive sugar intake and diseases accompanied by obesity have become a serious health issue. Accordingly, the development of low-calorie sweeteners (sweetening agents) as sugar replacers has been strongly in demand. As a sweetener that is widely used at present, there is aspartame which is excellent in safety and quality of sweetness, but however, is somewhat problematic in stability.

Against this background, N-[N-[3-(3-methyl-4-hydroxyphenyl)-3-methylbutyl]-L-α-aspartyl]-L-phenylalanine 1-methyl ester has been found to be a sweetener which has excellent stability and moreover is better by far in regard to the degree of sweetness, i.e., affords an advantage in regard to cost per sweet taste, by some of the present inventors and the like.

N-[N-[3-(3-methyl-4-hydroxyphenyl)-3-methylbutyl]-L-α-aspartyl]-L-phenylalanine 1-methyl ester may be prepared by reductively alkylating β-O-benzyl-α-L-aspartyl-L-phenylalanine methyl ester with 3-(3-methyl-4-benzyloxyphenyl)-3-methylbutyl aldehyde and NaB(OAc)$_3$H, followed by removing the benzyl group protecting group therefrom. However, 3-(3-methyl-4-benzyloxyphenyl)-3-methylbutyl aldehyde is synthesized from 3-methyl-4-hydroxyacetophenone in a seven-stage process which involves many reaction steps, as shown in the following Reaction Process 1. Accordingly, it is difficult to say that 3-(3-methyl-4-benzyloxyphenyl)-3-methylbutyl aldehyde is an industrially profitable starting material, because of the complicated reaction process for its synthesis.

Reaction Process 1:

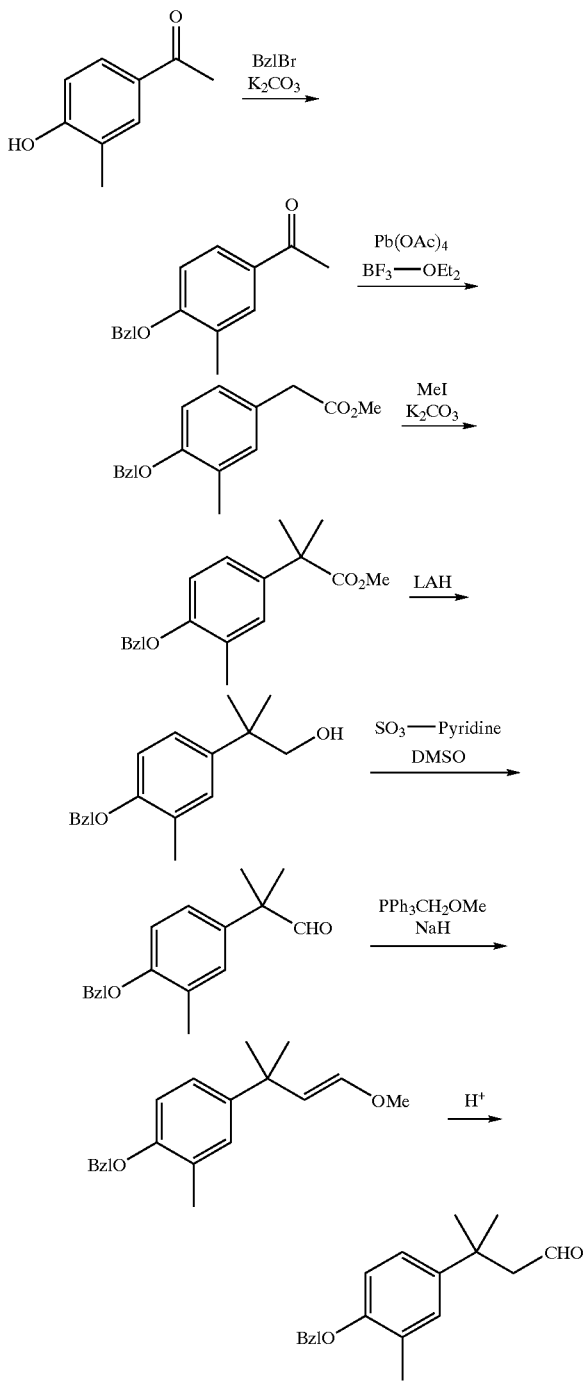

Wherein BzlBr represents benzyl bromide, Bzl represents a benzyl group, LAH represent lithium aluminum hydride, and DMSO represents dimethyl sulfoxide.

Thus, there remains a need for a process for producing industrially and efficiently N-[N-[3-(3-methyl-4-hydroxyphenyl)-3-methylbutyl]-L-α-aspartyl]-L-phenylalanine 1-methyl ester, which is excellent as a sweetener and has a high potency of sweetness. There also remains a need for production intermediates which are useful for producing N-[N-[3-(3-methyl-4-hydroxyphenyl)-3-methylbutyl]-L-α-aspartyl]-L-phenylalanine 1-methyl ester. There also remains a need for methods for producing such production intermediates.

SUMMARY OF THE INVENTION

Accordingly, it is one object of the present invention to provide novel compounds which are useful as intermediates for the production of N-[N-[3-(3-methyl-4-hydroxyphenyl)-3-methylbutyl]-L-α-aspartyl]-L-phenylalanine 1-methyl ester.

It is another object of the present invention to provide novel methods for preparing such intermediates.

There also remains a need for novel methods for producing N-[N-[3-(3-methyl-4-hydroxyphenyl)-3-methylbutyl]-L-α-aspartyl]-L-phenylalanine 1-methyl ester from such intermediates.

These and other objects, which will become apparent during the following detailed description, have been achieved by the inventors' discovery that N-[N-[3-(3-methyl-4-hydroxyphenyl)-3-methylbutyl]-L-α-aspartyl]-L-phenylalanine 1-methyl ester may be conveniently synthesized from new arylpropyl aldehyde derivatives, in particular 3-(3-methyl-4-hydroxyphenyl)-3-methylbutyl aldehyde. Thus, the present inventors have found certain new arylpropyl aldehyde derivatives, particularly 3-(3-methyl-4-hydroxyphenyl)-3-methylbutyl aldehyde, which are extremely useful for the production of the sweetener having a high potency of sweetness described above.

In addition, the inventors have discovered convenient methods for producing such arylpropyl aldehyde derivatives, particularly 3-(3-methyl-4-hydroxyphenyl)-3-methylbutyl aldehyde. One preferred embodiment of an efficient process for production of 3-(3-methyl-4-hydroxyphenyl)-3-methylbutyl aldehyde is shown in the following Reaction Process 2. According to this embodiment, 3-(3-methyl-4-hydroxyphenyl)-3-methylbutyl aldehyde can be synthesized by a reaction process having a total of only three stages, which comprises: (1) reacting 2-methoxytoluene with 3-methylcrotonic acid, preferably in the presence of an acid (first stage); (2) converting the methoxy group in the butyric acid thus obtained to a hydroxyl group, preferably through an acid hydrolysis (second stage); and (3) finally converting the carboxylic acid thus obtained to an aldehyde (third stage). Accordingly, with respect to the production of the production intermediates, the present process is industrially advantageous (is superior to) in comparison with the process which uses 3-(3-methyl-4-benzyloxyphenyl)-3-methylbutyl aldehyde as an production intermediate, because of the complicated synthesis of 3-(3-methyl-4-benzyloxyphenyl)-3-methylbutyl aldehyde, which requires seven stages of many reaction steps as described above.

In addition, the present inventors have found that the compound also is industrially excellent as an intermediate for the production of N-[N-[3-(3-methyl-4-hydroxyphenyl)-3-methylbutyl]-L-α-aspartyl]-L-phenylalanine 1-methyl ester. These findings have led to the completion of the present invention.

Reaction Process 2:

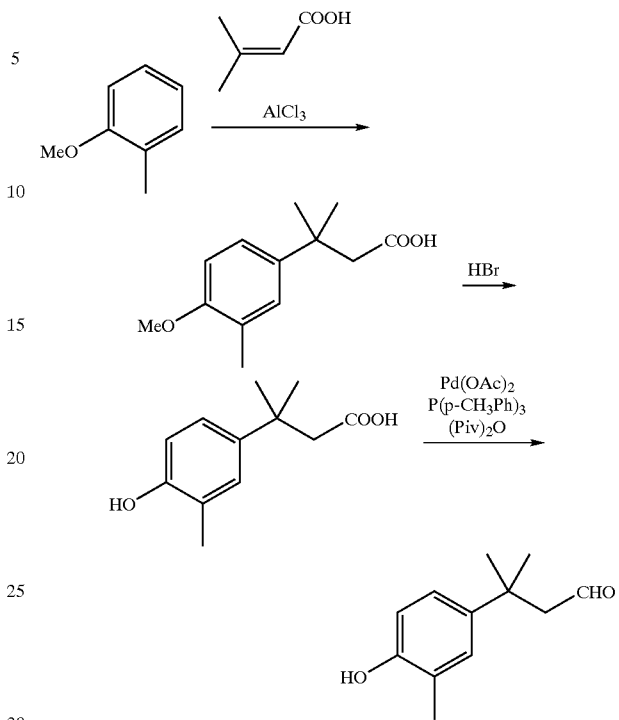

Where Piv represents a pivaloyl group and (Piv)$_2$O represents pivalic acid anhydride.

Thus, in a first embodiment, the present invention provides a process for producing 3-(3-methyl-4-hydroxyphenyl)-3-methylbutyl aldehyde, which comprises:
    subjecting 3-(3-methyl-4-hydroxyphenyl)-3-methylbutyric acid to a reaction for converting a carboxyl group into a formyl group.

In a preferred embodiment, the present invention provides a process for producing 3-(3-methyl-4-hydroxyphenyl)-3-methylbutyl aldehyde, which comprises:
    subjecting 3-(3-methyl-4-hydroxyphenyl)-3-methylbutyric acid to a reaction for converting a carboxyl group into a formyl group,
    wherein said 3-(3-methyl-4-hydroxyphenyl)-3-methylbutyric acid is obtained by subjecting 3-(3-methyl-4-methoxyphenyl)-3-methylbutyric acid to a reaction for converting a methoxy group into a hydroxyl group.

In another preferred embodiment, the present invention provides a process for producing 3-(3-methyl-4-hydroxyphenyl)-3-methylbutyl aldehyde, which comprises:
    subjecting 3-(3-methyl-4-hydroxyphenyl)-3-methylbutyric acid to a reaction for converting a carboxyl group into a formyl group,
    wherein said 3-(3-methyl-4-hydroxyphenyl)-3-methylbutyric acid is obtained by subjecting 3-(3-methyl-4-methoxyphenyl)-3-methylbutyric acid obtained through the reaction of 2-methoxytoluene with 3-methylcrotonic acid to a reaction for converting a methoxy group into a hydroxyl group.

In another preferred embodiment, the present invention provides a process for producing 3-(3-methyl-4-hydroxyphenyl)-3-methylbutyl aldehyde, which comprises:
    subjecting 3-(3-methyl-4-hydroxyphenyl)-3-methylbutyric acid to a reaction for converting a carboxyl group into a formyl group, wherein said 3-(3-methyl-4-hydroxyphenyl)-3-methylbutyric acid is obtained by subjecting 3-(3-methyl-4-methoxyphenyl)-3-methylbutyric acid obtained through the reaction of 2-methoxytoluene with 3-methylcrotonic acid to a reaction for converting a methoxy group into a hydroxyl group, wherein said reaction of 2-methoxytoluene with 3-methylcrotonic acid is conducted in the presence of an acid.

In another preferred embodiment, the present invention provides a process for producing 3-(3-methyl-4-hydroxyphenyl)-3-methylbutyl aldehyde, which comprises:
  subjecting 3-(3-methyl-4-hydroxyphenyl)-3-methylbutyric acid to a reaction for converting a carboxyl group into a formyl group, wherein said reaction for converting a carboxyl group into a formyl group is any one of the following reactions:
    (a) a reaction for converting a carboxylic acid to an aldehyde through reduction thereof, and
    (b) a reaction for converting a carboxyl group into a hydroxymethyl group, and thereafter converting the hydroxymethyl group into a formyl group.

In another embodiment, the present invention provides a process for producing N-[N-[3-(3-methyl-4-hydroxyphenyl)-3-methylbutyl]-L-α-aspartyl]-L-phenylalanine 1-methyl ester, which comprises:
  subjecting 3-(3-methyl-4-hydroxyphenyl)-3-methylbutyl aldehyde and aspartame to a reductive alkylation reaction.

It is possible and advantageous to use directly the 3-(3-methyl-4-hydroxyphenyl)-3-methylbutyl aldehyde as it is, produced in the above processes, for the starting material of the reductive alkylation reaction for the production of N-[N-[3-(3-methyl-4-hydroxyphenyl)-3-methylbutyl]-L-α-aspartyl]-L-phenylalanine 1-methyl ester.

In another embodiment, the present invention provides novel compounds represented by the following general formula (1):

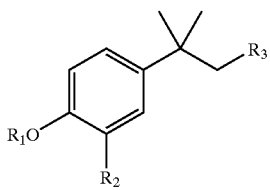

(1)

wherein $R_1$ represents a hydrogen atom or a lower alkyl group having 1 to 4 carbon atoms, $R_2$ represents a lower alkyl group having 1 to 4 carbon atoms, and $R_3$ represents any one of a carboxyl group, a formyl group, or a hydroxymethyl group.

In a particularly preferred embodiment, the present invention provides the following compounds (a to f) which are particularly preferable as production intermediates:
  a. 3-(3-methyl-4-hydroxyphenyl)-3-methylbutyl aldehyde;
  b. 3-(3-methyl-4-methoxyphenyl)-3-methylbutyric acid;
  c. 3-(3-methyl-4-hydroxyphenyl)-3-methylbutyric acid;
  d. 3-(3-methyl-4-hydroxyphenyl)-3-methyl-1-butanol;
  e. 3-(3-methyl-4-methoxyphenyl)-3-methylbutyl aldehyde; and
  f. 3-(3-methyl-4-methoxyphenyl)-3-methyl-1-butanol.

DETAILED DESCRIPTION OF THE PREFERRED EMBODIMENTS

Thus, in a first embodiment, the present invention provides novel methods for preparing 3-(3-methyl-4-hydroxyphenyl)-3-methylbutyl aldehyde.

In the following description, the process for production of 3-(3-methyl-4-hydroxyphenyl)-3-methylbutyl aldehyde is explained in detail by reference to the preferred example shown above in Reaction Process 2. However, the reaction scheme is but one particularly preferred example of the present method, and the present invention is not limited to the example shown in Reaction Process 2.

Starting with 2-methoxytoluene with 3-methylcrotonic acid, the first stage shown in Reaction Process 2 is the reaction of 2-methoxytoluene with 3-methylcrotonic acid in the above first stage, which can be conducted either with or without a solvent. However the reaction of 2-methoxytoluene with 3-methylcrotonic acid is preferably conducted in an organic solvent in the presence of an acid. As for the organic solvent, if employed, there is no special limitation thereto, as long as the solvent is inactive to the staring materials, any acid used, and the reaction product.

In case when an acid is employed, any acid, such as a proton acid, such as sulfuric acid, p-toluenesulfonic acid, and hydrogen chloride, or a Lewis acid, such as aluminum chloride and titanium tetrachloride, and the like, can be employed. A combination of two or more acids may be employed, respectively as the proton acid or the Lewis acid, if necessary. Further, as the case may be, a proton acid can be employed in combination with a Lewis acid, such as combination of hydrogen chloride with aluminum chloride, if necessary. In addition, an acid fixed on the surface of a solid phase or support may be desirably employed, because the process for treatment may be simplified.

The amount of acid to be employed is not particularly limited. In case when a large excess of acid, based on the 3-methylcrotonic acid, is employed, the reaction can be conducted to completion in a shorter time. From the economical point of view, preferably 5 molar equivalents or less, more preferably 3 molar equivalents or less, and further more preferably 0.1 to 3 molar equivalents or so, of the acid, based on the number of moles of the 3-methylcrotonic acid, may be employed.

The ratio of the 2-methoxytoluene used to the 3-methylcrotonic acid is not particularly limited. Preferably, the 2-methoxytoluene is used in an amount of 0.5 molar equivalents or more, more preferably 1 molar equivalent or more, and further more preferably 1 to 10 molar equivalents or so, based on the moles of the 3-methylcrotonic acid.

As for a reaction temperature, there is no particular limitation thereto. The higher the reaction temperature is, the more the secondary reaction proceeds, and at a low temperature, the reaction speed becomes slow to an extreme. Accordingly, a temperature range of, preferably −20 to 180° C. or so, and more preferably −10 to 100° C. or so, and further more preferably 0 to 70° C. or so, is employed.

In the second stage of Reaction Process 2, the methoxy group in the 3-(3-methyl-4-methoxyphenyl)-3-methylbutyric acid obtained in the first stage is converted into a hydroxyl group. The conversion of the methoxy group into a hydroxyl group may be easily carried out, for example, by heating 3-(3-methyl-4-methoxyphenyl)-3-methylbutyric acid in an acidic aqueous solution. For the acid, if employed, hydrogen chloride, hydrogen bromide, sulfuric acid and the like may be used. There is no particular limitation to the reaction temperature therefor. A temperature range of 80 to 150° C. or so is preferably employed.

In the third stage of Reaction Process 2, the carboxyl group in the 3-(3-methyl-4-hydroxyphenyl)-3-methylbutyric acid obtained in the above reaction is converted into a formyl group. In order to produce the aldehyde from 3-(3-methyl-4-hydroxyphenyl)-3-methylbutyric acid, the carboxylic acid may be subjected directly to a reaction for the reduction of the carboxyl group therein, whereby the objective 3-(3-methyl-4-hydroxyphenyl)-3-methylbutyl aldehyde can be obtained. In this case, the carboxylic acid can be preferably reduced directly, based on the process described in *Chemistry Letters*, pp. 1143–1144, published in 1998, November, to afford the objective 3-(3-methyl-4-hydroxyphenyl)-3-methylbutyl aldehyde. This process involves reducing the 3-(3-methyl-4-hydroxyphenyl)-3-methylbutyric acid with hydrogen in an organic solvent, with pivalic acid anhydride, palladium acetate and triphenylphosphine derivative added thereto. As for the organic solvent, there is no particular limitation thereto, as long as the solvent is inert to the starting materials (substrates) for reaction, any catalyst, and the product. For example, acetone, tetrahydrofuran (THF), toluene, and the like may be preferably employed.

If employed, the pivalic acid anhydride may be used in an amount which is equimolar or more based on the moles of 3-(3-methyl-4-hydroxyphenyl)-3-methylbutyric acid. For example, the pivalic acid anhydride may be used in an amount of 1 to 5 moles or so to 1 mole of 3-(3-methyl-4-hydroxyphenyl)-3-methylbutyric acid. As the triphenylphosphine derivative, if employed, triphenylphosphine and tri-tolylphosphine may be preferably employed.

The palladium acetate and triphenylphosphine derivative may be used as a catalyst, and therefore a few molar % or so thereof is sufficient for the quantities employed thereof. As for a reaction temperature employed in the reaction, there is no particular limitation thereto. At higher temperatures, the reaction is promoted, and thus can be completed and finished in a short time. Accordingly, it may be conducted at an advantage at a comparatively high temperature.

Alternatively, rather than producing the aldehyde by direct reduction of the carboxylic acid, the carboxyl group may be first reduced completely to a hydroxymethyl group, and thereafter partially oxidized to produce the above aldehyde derivative. In this case, the above object compound can be easily produced, with the use of reduction—partial oxidation, which in itself is known (see, *Journal of Organic Chemistry*, vol. 48, No. 25, pp. 5043–5048 (1983)).

Incidentally, in the production of the above aldehyde derivative, the process for converting a methoxy group into a hydroxyl group, firstly from 3-(3-methyl-4-methoxyphenyl)-3-methylbutyric acid, to produce 3-(3-methyl-4-hydroxyphenyl)-3-methylbutyric acid, followed by a reaction to produce the aldehyde, was explained above. Alternatively, the reaction for converting the methoxy group into the hydroxyl group can be conducted after the above reduction (formylation) of the butyric acid derivative or the reduction thereof (hydroxymethylation), in the same manner as described above.

For example, by the above-described partial reduction (formylation) or the above-described more complete reduction (hydroxymethylation) of 3-(3-methyl-4-methoxyphenyl)-3-methylbutyric acid, 3-(3-methyl-4-methoxyphenyl)-3-methylbutyl aldehyde, or 3-(3-methyl-4-methoxyphenyl)-3-methyl-1-butanol, repectively, can be also produced.

The production of N-[N-[3-(3-methyl-4-hydroxyphenyl)-3-methylbutyl]-L-α-aspartyl]-L-phenylalanine 1-methyl ester from the 3-(3-methyl-4-hydroxyphenyl)-3-methylbutyl aldehyde thus obtained can be achieved without any particular difficulty. N-[N-[3-(3-methyl-4-hydroxyphenyl)-3-methylbutyl]-L-α-aspartyl]-L-phenylalanine 1-methyl ester can be easily produced by reductively alkylating this aldehyde with α-L-aspartyl-L-phenylalanine methyl ester (aspartame) under hydrogenation conditions (hydrogen addition). Specifically, the reductive alkylation of 3-(3-methyl-4-hydroxyphenyl)-3-methylbutyl aldehyde with α-L-aspartyl-L-phenylalanine methyl ester (aspartame) may be carried out in any solvent which can dissolve the starting materials, for example, acetonitrile, acetic acid, ethyl acetate, alcohol, water-alcohol mixtures, or the like, in the presence of a catalyst for reductive alkyaltion, for example, a catalysts for hydrogenation such as palladium based catalyst, rhodium based catalyst and the like. The reductive alkylation reaction is conducted with hydrogen, more preferably, under suitable or effective reaction temperature and pressure to produce the above object compound, N-[N-[3-(3-methyl-4-hydroxyphenyl)-3-methylbutyl]-L-α-aspartyl]-L-phenylalanine 1-methyl ester.

From the reaction mixture thus obtained, the catalyst used may be removed, and the remaining material may subjected to purification step(s), such as a purification with a chromatography, a crystallization step and the like, if required, whereby a high purity of the desired aspartyl dipeptide ester derivative, N-[N-[3-(3-methyl-4-hydroxyphenyl)-3-methylbutyl]-L-α-aspartyl]-L-phenylalanine 1-methyl ester, a sweetener having a high potency of sweetness described above can be separated.

Other features of the invention will become apparent in the course of the following descriptions of exemplary embodiments which are given for illustration of the invention and are not intended to be limiting thereof.

EXAMPLES

Example 1

Synthesis of 3-(3-methyl-4-methoxyphenyl)-3-methylbutyric acid

To 2-methoxytoluene (146.7 g, 1.2 mol), aluminum chloride (44 g, 0.33 mol) and 3-methylcrotonic acid (30 g, 0.3 mol) were added, and the mixture was stirred at room temperature for 24 hours, and thereafter the reaction was stopped by the addition of six normal (6-N) hydrochloric acid aqueous solution (300 ml) thereto. Subsequently, from the thus-obtained mixture, the organic material was extracted with diethyl ether (150 ml). After that, one normal (1-N) caustic soda aqueous solution (100 ml) was added to the organic layer for extraction of the carboxylic acid(s). The thus-obtained alkaline mixture was acidified by the addition of hydrochloric acid (HCl) aqueous solution, and the mixture was extracted with diethyl ether and the solvent therein was removed by distillation. The thus-obtained residue was re-crystallized with hexane to obtain 3-(3-methyl-4-methoxyphenyl)-3-methylbutyric acid (39.6 g, yield: 59%). $^1$H NMR (CDCl$_3$) δ: 1.43 (s, 6H), 2.21 (s, 3H), 2.61 (s, 2H), 3.80 (s, 3H), 6.74–6.77 (dd, 1H), 7.12–7.15 (m, 2H).

Example 2

Synthesis of 3-(3-methyl-4-hydroxyphenyl)-3-methylbutyric acid 3-(3-Methyl-4-methoxyphenyl)-3-methylbutyric acid (11.1 g, 0.05 mol), acetic acid (22.3 g), and 48% hydrobromic acid aqueous solution (33.7 g, 0.2 mol) were mixed together, and stirred for 4 hours at 120° C. The mixture was cooled to room temperature, and the thus-obtained reaction solution was extracted with diethyl ether. The organic layer was washed with sodium chloride saturated aqueous solution, and then the solvent was removed by distillation to obtain 3-(3-methyl-4-hydroxyphenyl)-3-methylbutyric acid (10 g, yield: 95%).
$^1$H NMR (CDCl$_3$) δ: 1.42 (s, 6H), 2.21 (s, 3H), 2.60 (s, 2H), 6.60–6.65 (dd, 1H), 6.99–7.10 (m, 2H).

Example 3

Synthesis of 3-(3-methyl-4-hydroxyphenyl)-3-methylbutyl aldehyde

Into a chemical reactor for hydrogen addition (hydrogenation) under elevated pressure, 3-(3-methyl-4-hydroxyphenyl)-3-methylbutyric acid (9.38 g, 0.045 mol), pivalic acid anhydride (16.8 g, 0.09 mol) and acetone (90 ml) were filled, and thereafter the reactor was deaerated. Subsequently, a tetrahydrofuran (THF) solution (4.5 ml) of palladium acetate (101 mg, 0.45 mmol) and tri-p-tolylphosphine (685 mg, 2.25 mmol) produced previously, was added thereto, and the mixture was stirred under hydrogen pressure of 5 MPa at 80° C. for 24 hours for reaction.

Acetone was removed from the reaction solution by distillation, and the thus-obtained residue was purified by the use of vacuum distillation to obtain 3-(3-methyl-4-hydroxyphenyl)-3-methylbutyl aldehyde (4.82 g, yield: 56%). Boiling point (b.p.): 136° C. (1 mmHg[133Pa]).
$^1$H NMR (CDCl$_3$) δ: 1.42 (s, 6H), 2.24 (s, 3H), 2.62 (d, 2H), 5.13 (s, 1H), 6.70–6.73 (dd, 1H), 7.03–7.11 (m, 2H), 9.49 (t, 1H).

Example 4

Synthesis of N-[N-[3-(3-methyl-4-hydroxyphenyl)-3-methylbutyl]-L-α-aspartyl]-L-phenylalanine 1-methyl ester Aspartame (5.89 g, 20.0 mmol) and 3-(3-methyl-4-hydroxyphenyl)-3-methylbutyl aldehyde (3.202 g, 16.7 mmol) were added to 80% methanol aqueous solution (200 ml), and the mixture was stirred at 40° C. for a short time. To this solution, 10% palladium on activated carbon having a water content of 50% (1.78 g) was added, and the mixture was stirred under a hydrogen atmosphere of normal pressure (0.1 MPa) at 25° C. for 40 hours. The thus-obtained reaction solution was filtered to remove the catalyst, and the filtrate was subjected to high performance liquid chromatography (HPLC), and it was thereby determined that the title compound was produced (7.06 g, 15.03 mmol, 90%).

Effect of Invention

By using the novel 3-(3-methyl-4-hydroxyphenyl)-3-methylbutyl aldehyde as the production intermediate in the present invention, in a reductive alkylation reaction with aspartame, N-[N-[3-(3-methyl-4-hydroxyphenyl)-3-methylbutyl]-L-α-aspartyl]-L-phenylalanine 1-methyl ester, which is useful as a sweetener having a high potency of sweetness, can be produced easily and efficiently on an industrial scale.

The aldehyde derivative described above is a novel compound, and can be produced easily and efficiently in a process involving subjecting 3-(3-methyl-4-methoxyphenyl)-3-methylbutyric acid obtained through the reaction of 2-methoxytoluene with 3-methylcrotonic acid, to a reaction for converting a methoxy group into a hydroxyl group to produce a carboxylic acid, followed by a reaction for converting a carboxyl group of the carboxylic acid thus obtained into a formyl group. Therefore, according to the present invention, the sweetener having a high potency of sweetness described above, N-[N-[3-(3-methyl-4-hydroxyphenyl)-3-methylbutyl]-L-α-aspartyl]-L-phenylalanine 1-methyl ester, can be produced advantageously on an industrial scale.

Also, there are provided several novel compounds which are useful as production intermediates, such as the aldehyde derivative described above and the like.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

What is claimed is:

1. A process for producing 3-(3-methyl-4-hydroxyphenyl)-3-methylbutyl aldehyde, which comprises:
   converting a carboxyl group of 3-(3-methyl-4-hydroxyphenyl)-3-methylbutyric acid into a formyl group.

2. The process of claim 1, wherein said 3-(3-methyl-4-hydroxyphenyl)-3-methylbutyric acid is prepared by converting a methoxyl group of 3-(3-methyl-4-methoxyphenyl)-3-methylbutyric acid into a hydroxyl group.

3. The process of claim 1, wherein said 3-(3-methyl-4-hydroxyphenyl)-3-methylbutyric acid is prepared by:
   (1) reacting 2-methoxytoluene with 3-methylcrotonic acid, to obtain 3-(3-methyl-4-methoxyphenyl)-3-methylbutyric acid; and
   (2) converting a methoxy group of 3-(3-methyl-4-methoxyphenyl)-3-methylbutyric acid into a hydroxyl group.

4. The process of claim 3, wherein said reaction of 2-methoxytoluene with 3-methylcrotonic acid is conducted in the presence of an acid.

5. The process of claim 1, wherein said reaction for converting a carboxyl group into a formyl group is carried out by reducing a said carboxyl group to said formyl group.

6. The process of claim 1, wherein said reaction for converting a carboxyl group into a formyl group is carried out by:
   (1) reducing said carboxyl group into a hydroxymethyl group; and
   (2) converting said hydroxymethyl group into said formyl group.

7. A process for producing N-[N-[3-(3-methyl-4-hydroxyphenyl)-3-methylbutyl]-L-α-aspartyl]-L-phenylalanine 1-methyl ester, which comprises:
   reductive alkylating 3-(3-methyl-4-hydroxyphenyl)-3-methylbutyl aldehyde with aspartame.

8. The process of claim 7, wherein said 3-(3-methyl-4-hydroxyphenyl)-3-methylbutyl aldehyde is prepared by a process which comprises:
   converting a carboxyl group of 3-(3-methyl-4-hydroxyphenyl)-3-methylbutyric acid into a formyl group.

9. The process of claim 8, wherein said 3-(3-methyl-4-hydroxyphenyl)-3-methylbutyric acid is prepared by converting a methoxyl group of 3-(3-methyl-4-methoxyphenyl)-3-methylbutyric acid into a hydroxyl group.

10. The process of claim 8, wherein said 3-(3-methyl-4-hydroxyphenyl)-3-methylbutyric acid is prepared by:
    (1) reacting 2-methoxytoluene with 3-methylcrotonic acid, to obtain 3-(3-methyl-4-methoxyphenyl)-3-methylbutyric acid; and
    (2) converting a methoxy group of 3-(3-methyl-4-methoxyphenyl)-3-methylbutyric acid into a hydroxyl group.

11. The process of claim 10, wherein said reaction of 2-methoxytoluene with 3-methylcrotonic acid is conducted in the presence of an acid.

12. The process of claim 8, wherein said reaction for converting a carboxyl group into a formyl group is carried out by reducing a said carboxyl group to said formyl group.

13. The process of claim 8, wherein said reaction for converting a carboxyl group into a formyl group is carried out by:
   (1) reducing said carboxyl group into a hydroxymethyl group; and
   (2) converting said hydroxymethyl group into said formyl group.

14. A compound having the following formula (1):

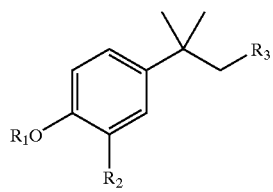

(1)

wherein $R_1$ represents a hydrogen atom or a lower alkyl group having 1 to 4 carbon atoms, $R_2$ represents a lower alkyl group having 1 to 4 carbon atoms, and $R_3$ represents a carboxyl group, a formyl group, or a hydroxymethyl group.

15. The compound of claim 14, wherein $R_1$ represents a hydrogen atom.

16. The compound of claim 14, wherein $R_1$ represents a methyl group.

17. The compound of claim 14, wherein $R_2$ represents a methyl group.

18. The compound of claim 14, wherein $R_3$ represents a formyl group.

19. The compound of claim 14, wherein $R_3$ represents a carboxyl group.

20. The compound of claim 14, which is selected from the group consisting of 3-(3-methyl-4-hydroxyphenyl)-3-methylbutyl aldehyde; 3-(3-methyl-4-methoxyphenyl)-3-methylbutyric acid; 3-(3-methyl-4-hydroxyphenyl)-3-methylbutyric acid; 3-(3-methyl-4-hydroxyphenyl)-3-methyl-1-butanol; 3-(3-methyl-4-methoxyphenyl)-3-methylbutyl aldehyde; and 3-(3-methyl-4-methoxyphenyl)-3-methyl-1-butanol.

* * * * *